United States Patent [19]
Norton

[11] Patent Number: 4,967,602
[45] Date of Patent: Nov. 6, 1990

[54] PNEUMATIC STRENGTH TESTER FOR SHEET MATERIALS

[75] Inventor: Michael K. Norton, Los Gatos, Calif.

[73] Assignee: Measurex Corporation, Cupertino, Calif.

[21] Appl. No.: 347,147

[22] Filed: May 3, 1989

[51] Int. Cl.⁵ .............................................. G01N 3/00
[52] U.S. Cl. .................................................... 73/840
[58] Field of Search ..................... 73/840, 159, 862.48, 73/789, 826; 364/471

[56] References Cited

U.S. PATENT DOCUMENTS 3,160,002 12/1964 Lovette ............................ 73/840 X
4,735,092 4/1988 Kenny .................................. 73/840

FOREIGN PATENT DOCUMENTS 228908 7/1925 United Kingdom ................... 73/840

Primary Examiner—Jerry W. Myracle
Attorney, Agent, or Firm—Spensley Horn Jubas & Lubitz

[57] ABSTRACT

A device, system, and method for measuring the strength of a sheet material during or after the manufacturing process are described. The present invention forms a chamber having one wall consisting of the sheet material to be tested. A high pressure air supply feeds into a reservoir which is in flow communication with the chamber by way of a valve. High pressure air is injected into the chamber, and the sheet ruptures. A pressure transducer measures the pressure in the chamber. The pressure measurements are differentiated, and a peck detector detects the peak derivative value obtained and thus the time at which the sheet ruptured. A computer determines the pressure in the chamber at the time that the sheet ruptured.

18 Claims, 3 Drawing Sheets

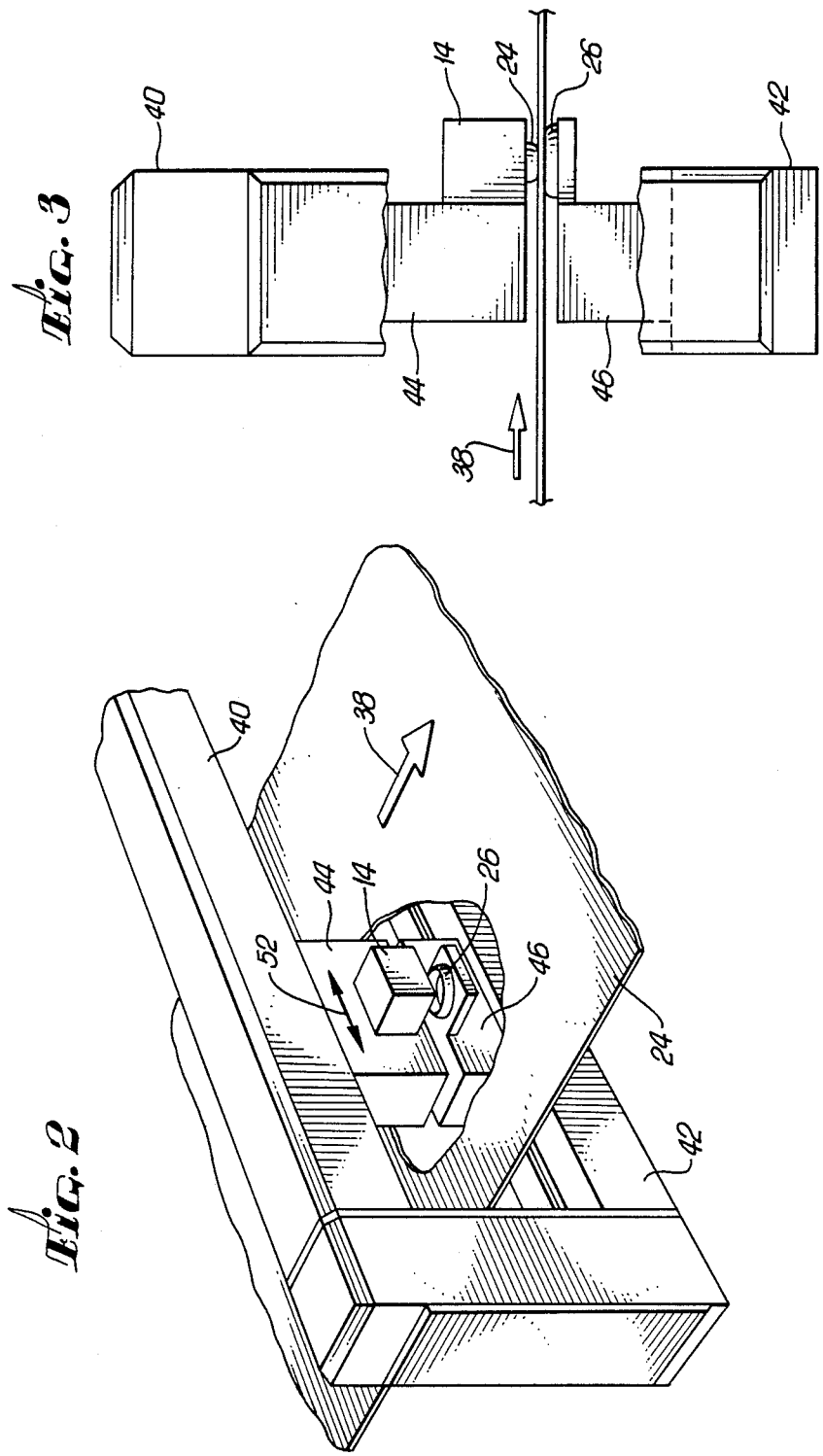

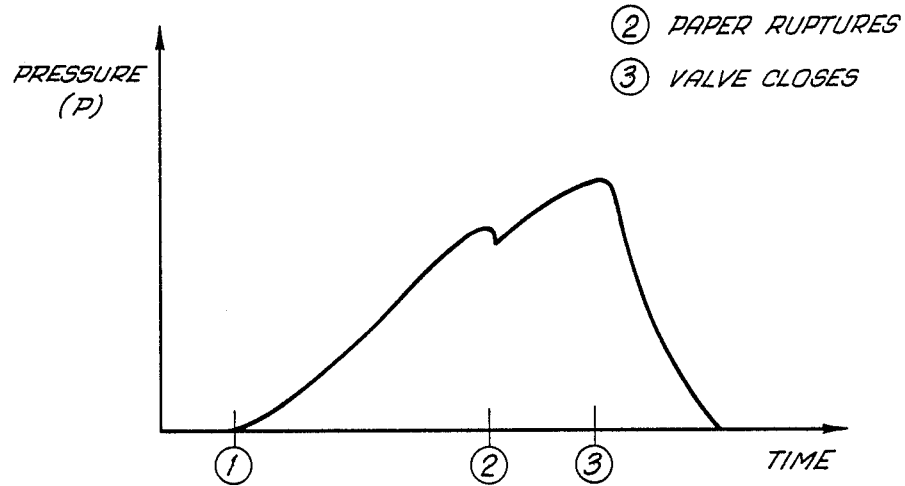
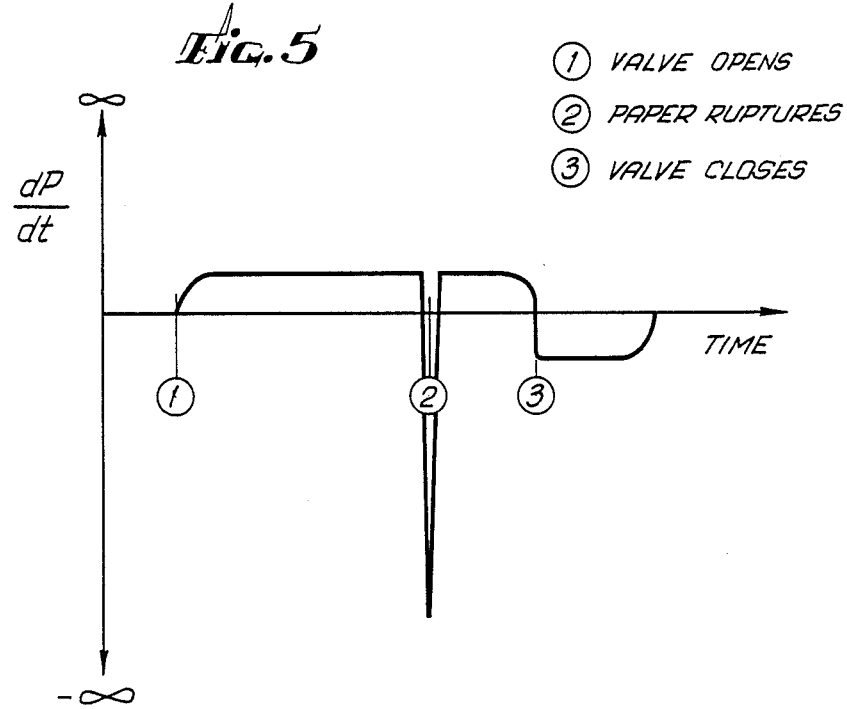

4,967,602

PNEUMATIC STRENGTH TESTER FOR SHEET MATERIALS

BACKGROUND OF THE INVENTION

The present invention relates to the strength testing of sheet materials, and more particularly to a pneumatic system having a high pressure air source which by way of a valve feeds into a chamber having one wall consisting of the sheet material to be tested. In general, the present invention relates to sheet materials. However, the following discussion refers to the specific sheet material of paper.

Paper is produced in various grades to suit various applications. It is, of course, important that paper be strong enough to perform its intended function. To ensure adequate strength, and thus satisfactory performance, paper sheets must be tested for strength.

Paper commonly is produced in bulk in a continuous sheet. The sheet is wound in reels at the end of the manufacturing process, and immediately after one reel is finished, another reel is begun. Often it is desirable to measure the strength of the paper during the manufacturing process, so that if paper strength is not satisfactory, process controls can be adjusted accordingly.

Prior art devices for measuring the strength of paper ruptured the paper by projecting a solid object through the plane of the paper. Such devices are not easily adapted to use during the manufacturing process, if at all, because the solid object remains projected through the plane of the paper and would continue to tear the paper sheet as the paper moves past the strength tester. These prior art devices cannot be used until after completion of the manufacturing process.

For instance, the Mullen test, also known as the burst pressure test, uses a rubber diaphragm and liquid pressure to rupture the paper. In this test, the paper sample is clamped between two circular clamping rings which have a specific standard inner diameter. A rubber diaphragm is placed on one side of the sheet sample, and liquid pressure is applied until the paper ruptures. The pressure required to rupture the paper is called the "burst pressure" and is commonly used in the paper industry to specify strength.

Since the prior art strength testers are not used until after completion of the manufacturing process, paper production is inefficient. If process controls require adjustment in order for strength requirements to be met, the need for this adjustment is not known until after the paper reel has been completely manufactured, and the sheet has been tested in the lab. This process is time-consuming and costly. Paper with inadequate strength characteristics continues to be produced until lab tests are made and process controls can be adjusted.

The present invention overcomes the disadvantages of the prior art, for it provides a means for measuring sheet strength during the manufacturing process.

SUMMARY OF THE INVENTION

The present invention relates to a device, system, and method suitable for quickly and easily testing the strength of a sheet material during the manufacturing process.

The pneumatic strength tester of the present invention has a high pressure reservoir in flow communication with a hollow member. A valve regulates the flow of high pressure gas from the reservoir to the hollow member. The sheet material being tested (for purposes of this discussion, paper) is positioned to contact the hollow member so as to form a sealed chamber. A high pressure gas supply feeds into the reservoir. Although a variety of gases can be used, for ease of discussion, reference to air will be made herein.

When a strength measurement of paper is to be made, the valve is actuated. When the valve opens, high pressure air is substantially instantaneously injected from the high pressure reservoir into one end of the chamber. Assuming the pressure is high enough, the high pressure air ruptures the paper sheet sealing the opposite end of the chamber. A pressure transducer measures the pressure in the chamber. Since the pressure in the chamber may continue to increase even after the paper ruptures, means for determining the pressure in the chamber at the time that the paper ruptured must be devised. One such means utilizes an analog-to-digital converter to digitize the analog pressure measurements from a pressure transducer. The digitized pressure measurements are transmitted to a computer which differentiates the pressure measurements with respect to time. The digitized pressure measurements are differentiated because the point on the pressure curve where the paper sheet ruptures will have a slope approaching infinity. Thus, the derivative value having the highest absolute magnitude in comparison to the first derivative of any other point on the pressure curve will occur at the point where the paper sheet ruptured. After a peak derivative value has been detected, a computer determines the rupture pressure of the paper sheet.

The device of the present invention may be attached to a scanning platform which moves back and forth across the width of the moving paper so that cross-directional strength measurements may be made during the manufacturing process.

BRIEF DESCRIPTION OF THE DRAWINGS

FIG. 2 is a perspective view of an embodiment of a pneumatic strength tester for sheet materials mounted to a scanning platform which scans back and forth across the width (i.e., cross-direction) of a moving sheet material.

FIG. 3 is a partially broken-away side view of the apparatus of FIG. 2.

FIG. 4 is a graphical depiction of a typical pressure curve likely to be obtained with an embodiment of a pneumatic strength tester for sheet materials.

FIG. 5 is a graphical depiction of the first derivative at each point of the pressure curve of FIG. 4.

DETAILED DESCRIPTION OF THE PREFERRED EMBODIMENT

Figure 1:
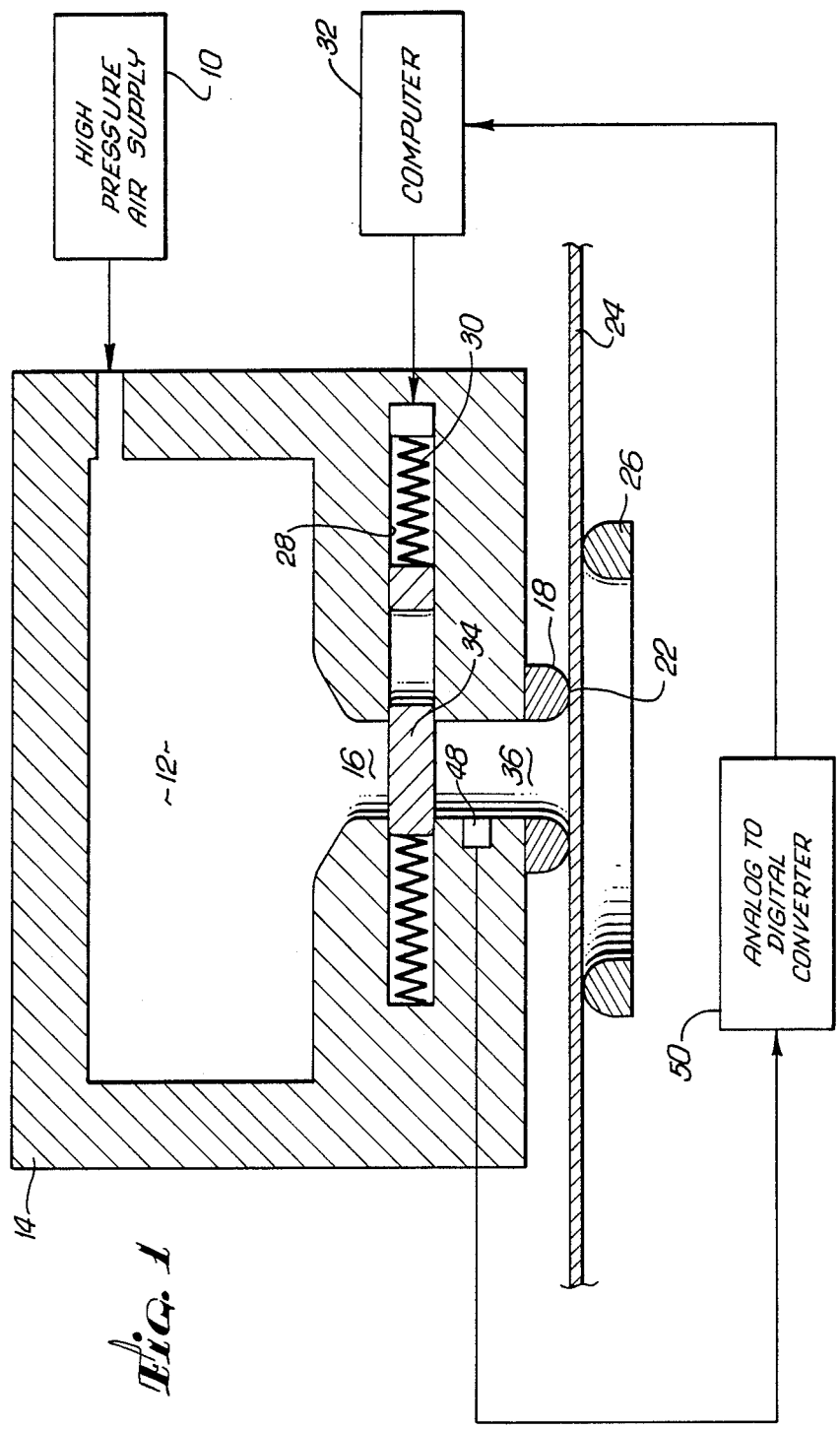
FIG. 1 is a cross-sectional view of an embodiment of a pneumatic strength tester for sheet materials with a schematic of the electronic components.

FIG. 1 illustrates a preferred embodiment of the present invention In this embodiment, a high pressure air supply 10 provides high pressure air to a reservoir 12 in a structure 14. The structure walls are capable of withstanding pressure of up to at least 1,000 psi.

The reservoir 12 narrows into a circular, vertical throat 16 in the structure 14. A sheet ring 18 is attached to the base of the structure 14 concentric with the throat 16. The surface of the sheet ring 18 placed in contact with the paper sheet 24 is made of a substantially abrasion resistant, substantially non-abrasive material such as smooth sapphire or tungsten carbide. The protruding end of the sheet ring 18 forms a convex surface 22 which contacts the paper sheet 24 as the paper sheet 24 travels past the strength tester. The paper sheet 24 is positioned so that the convex surface 22 of the sheet ring 18 pushes into the paper sheet 24 and forms a seal at the paper sheet 24 sheet ring 18 interface. A circular sheet positioning guide 26 having a hole therethrough contacts the underside of the paper sheet 24. The surface of the sheet positioning guide 26 placed in contact with the paper sheet 24 also is made of a substantially abrasion resistant, substantially non-abrasive material such as smooth sapphire or tungsten carbide.

A horizontal channel 28 is cut through the top end portion of the throat 16. The horizontal channel 28 accommodates a spring-loaded valve 30 which is actuated by a computer 32. A baffle portion 34 of the valve 30 obstructs the throat 16 when the valve 30 is closed, thus forming the chamber 36 adjacent to the reservoir 12. The volume of the chamber 36 can be from 1 $cm^3$ to 10 $cm^3$. The diameter of the chamber 36 preferably is approximately 1 cm. The valve 30 is preferably capable of fully opening within a few microseconds, e.g. 3 usec., to provide an "explosive" increase in pressure in the chamber 36. In many situations, however, substantially slower opening valves may also be acceptable. The valve 30 must simply open fast enough so that the chamber 36 pressurizes substantially faster than air can leak out from between the sheet 24 and the sheet ring 18 to provide a rapid increase in pressure within the chamber 36.

The volume of the reservoir 12 must be large enough to ensure that upon opening the valve 30, an adequate supply of high pressure gas is maintained in the reservoir 12 so that the chamber 36 repeatedly can be filled substantially instantaneously with high pressure air without a substantial drop in pressure in the reservoir 12. Thus, the volume of the reservoir 12 preferably is approximately ten times the magnitude of the volume of the chamber 36. For example, for a chamber 36 having a volume of 1 $cm^3$, the reservoir 12 volume is approximately 10 $cm^3$. For a chamber 36 having a volume of 10 $cm^3$, the reservoir 12 volume is approximately 100 $cm^3$.

Paper production involves laying a wet mass of wood pulp fibers onto a moving porous belt, drying the mass, and finally, calendering the resulting paper sheet to give the paper the desired paper finish and thickness. The strength tester of the present invention is most advantageously used to monitor the strength of a paper sheet after the final calendering step, and before the paper is rolled-up on the final reel at the end of the manufacturing process. Since the strength of the paper produced may vary across the width of the sheet, the strength tester preferably is mounted on a scanning platform as shown in FIG. 2. In this manner, the strength tester is moved across the width of the sheet in the cross-direction while the sheet is being fed out of the calender and onto the final reel.

FIG. 2 illustrates a scanning platform which, as noted above, is preferably located after the final calender rolls and before the final reel. In this figure, the paper sheet is shown passing through the scanning station in the direction of arrow 38 between two transverse beams 40 and 42. Upper and lower support members, 44 and 46, are mounted to the upper 40 and lower 42 beams, respectively. The paper sheet 24 is shown in FIG. 2 with a cut-out area so that the relationship between the support members, 44 and 46, can be seen. A motor (not shown) within the scanning system is coupled to and drives the support members, 44 and 46, back and forth, in the cross-direction as indicated by arrow 52 in a continuous scanning motion, keeping the support members, 44 and 46, in vertical alignment at all times.

Practicality dictates that strength testing of the paper sheet 24 be held to a minimum in order to avoid riddling the paper sheet 24 with holes. Thus strength tester measurements preferably are made only at the end of a reel. The strength measurements made across this one section of the paper sheet 24 preferably are displayed on the computer screen and the displayed strength profile may be considered representative of the strength profile of the entire reel because process conditions remain nearly constant during the time required to manufacture a single reel. If paper strength is unsatisfactory, then process controls can be adjusted so that the next reel of paper has adequate strength.

An operation of a preferred embodiment of the present invention will now be described. The convex surface 22 of the sheet ring 18 and the sheet positioning guide 26 are positioned above and below the paper sheet 24, respectively. Preferably, the sheet ring 18 is displaced along a horizontal plane from the sheet positioning guide 26 such that pinching of the paper sheet 24 between the sheet ring 18 and the sheet guide 26 does not result. For instance, if a portion of a paper sheet 24 which is thicker than the rest of the sheet 24 passes between the sheet ring 18 and the sheet guide 26, pinching likely will result if a portion of the sheet ring 18 is situated directly opposite a portion of the sheet guide 26. Also, vibrations may cause pinching if the sheet ring 18 and the sheet guide 26 are not suitably displaced.

The reservoir 12 is provided with high pressure air from the high pressure air supply 10, e.g., 800 psi. The computer 32 actuates the spring-loaded valve 30 so that the chamber 36 substantially instantaneously fills with high pressure air. The air supplied to the chamber 36 is at a pressure substantially higher than the highest expected strength of the paper sheet 24. Assuming that the pressure is sufficiently high, the paper sheet 24 ruptures If the strength of the paper sheet 24, the inner diameter of the chamber 36, and the air pressure are such that the pressure in the chamber 36 peaks just before the paper sheet 24 ruptures, then a pressure peak detector can be used to determine the rupture pressure of the paper sheet 24. However, the pressure in the chamber 36 may increase even after the paper sheet 24 ruptures, because high pressure air may be entering the chamber 36 from the reservoir 12 at a faster rate than it is exiting the chamber 36. Thus, alternative means for determining the pressure at which the paper sheet 24 ruptured must be devised.

The computer 32 regulates the opening of the valve 30. A piezoelectric pressure transducer 48 monitors the pressure in the chamber 36, and an analog-to-digital converter 50 digitizes the pressure measurements. The digitized pressure measurements are then input to the computer 32 which calculates the first derivative with respect to time at each digitized pressure reading. As shown in FIG. 4, the point on the pressure curve where the paper sheet 24 ruptures will have a slope approaching infinity. Thus, as FIG. 5 shows, the derivative value having the highest absolute magnitude in comparison to the first derivative of any other point on the pressure curve will occur at the point where the paper sheet 24 ruptured. Depending upon the equipment used, the first derivative of a pressure measured at the time that the sheet 24 ruptured may be either a positive or a negative quantity. The pressure at which the sheet 24 ruptured is determined upon the basis of the derivative value having the highest absolute magnitude. For ease of discussion, reference to a "peak derivative value" will be made herein. This term describes the first derivative value having the highest absolute magnitude in comparison to the first derivative of any other point on the pressure curve. The computer 32 determines the peak derivative value and then the pressure in the chamber 36 at the time that the peak derivative value was obtained.

A preferred embodiment of the present invention has been described above. It is understood that one may make various modifications to the disclosed embodiment without departing from the spirit and scope of the invention. For instance, it is not necessary that the sheet ring 18 and the sheet positioning guide 26 be circular in shape. Sheet positioning means of other shapes could be used. Also, the means by which the rupture pressure is determined need not use a system comprising an analog-to-digital converter, differentiating means, peak detecting means, and computing means. For example, the pressure transducer could be coupled to a printer which prints out the pressure curve. By visually inspecting the curve, one could determine the rupture pressure of the paper sheet. In addition, the present invention may be used to test the strength of a stationary sheet after the completion of the manufacturing process as well as the strength of a rapidly moving sheet during the manufacturing process. Furthermore, the present invention may be used to test the strength of sheet materials other than paper. Thus, the present invention is not limited to the preferred embodiment described herein, but may be altered in a variety of ways which will be apparent to persons skilled in the art.

We claim:

1. A device for testing the strength of a moving sheet material, comprising:
   a gas reservoir having a throat therein;
   a valve disposed at the reservoir throat to regulate the flow of gas from the reservoir;
   a hollow member having a first hole at a first end thereof and a second hole at a second end thereof in flow communication with the first hole, the first hole being disposed adjacent to the valve to receive a flow of gas from the reservoir, the second end being adapted for slidable contact with one side of the moving sheet material;
   means for measuring gas pressure in the hollow member; and
   a sheet positioning guide having a hole therethrough, the sheet positioning guide being spaced from and disposed opposite the second end, so that the sheet material can move freely relative to the second end and the sheet positioning guide during testing.

2. A device for testing the strength of a sheet material as in claim 1, wherein the means for measuring pressure produces analog signals indicative of the pressure in the hollow member, the device further comprising means operatively coupled to the pressure measuring means for determining sheet strength based on the analog signal produced at the time the sheet ruptured.

3. A device for testing the strength of a sheet material as in claim 2, wherein the means for determining sheet strength comprises:
   a computer operatively coupled to the valve to regulate the flow of gas from the reservoir;
   an analog-to-digital converter operatively coupled to the pressure measuring means to digitize the analog signals of the pressure measuring means;
   a differentiating means operatively coupled to the analog-to-digital converter to compute a derivative of each digitized pressure measurement;
   a peak detecting means operatively coupled to the differentiating means to detect a peak derivative value computed by the differentiating means; and
   a computing means operatively coupled to the differentiating means to determine the pressure in the hollow member at the time at which the peak derivative value detected by the peak detecting means was obtained.

4. A device for testing the strength of a sheet material as in claim 1, wherein a sheet ring is attached to the end of the hollow member having the second hole so as to be concentric therewith, and the sheet ring and the sheet positioning guide each have a substantially non-abrasive, substantially abrasion-resistant sheet contacting surface.

5. A device for testing the strength of a sheet material as in claim 1, further comprising means for providing high pressure gas to the reservoir.

6. A device for testing the strength of a sheet material as in claim 5, wherein the means for providing high pressure gas to the reservoir includes a high pressure air source.

7. A system for testing the strength of a sheet material, comprising:
   a chamber having one wall consisting of the sheet material to be strength tested;
   means for providing a rapid increase in gas pressure in the chamber; and
   means for measuring the pressure in the chamber.

8. A system for testing the strength of a sheet material as in claim 7, wherein the high pressure gas providing means comprises:
   a high pressure gas source;
   a reservoir which receives high pressure gas from the high pressure gas source; and
   a valve which regulates the flow of gas between the reservoir and the chamber.

9. A system for testing the strength of a sheet material as in claim 7, wherein the pressure measuring means produces analog signals indicative of the pressure in the chamber, the device further comprising:
   an analog-to-digital converter operatively coupled to the pressure measuring means to digitize the analog signals of the pressure measuring means;
   a differentiating means operatively coupled to the analog-to-digital converter to compute a derivative of each digitized pressure measurement;
   a peak detecting means operatively coupled to the differentiating means to determine a peak derivative value computed by the differentiating means; and
   a computing means to determine the pressure in the chamber at the time that the peak derivative value detected by the peak detecting means was obtained.

10. A system for testing the strength of a sheet material as in claim 7, wherein the gas is air.

11. A method for testing the strength of a sheet material, comprising the steps of:
    injecting a burst of high pressure gas into a chamber having one wall thereof formed of the sheet pressure material to be strength tested; and measuring the pressure of the chamber at the time that the sheet ruptures.

12. A method for testing the strength of a sheet material as in claim 11, wherein the step of measuring the pressure in the chamber at the time that the sheet ruptures further comprises the step of producing analog signals indicative of the pressure in the chamber 13. A method for testing the strength of a sheet material as in claim 12, further comprising the steps of:
inputting the analog signals to an analog-to-digital converter to produce digitized pressure measurements, inputting the digitized pressure measurements to a differentiating means to compute a first derivative of each digitized pressure measurement, inputting the first derivative of each digitized pressure measurement to a peak detecting means to detect a peak derivative value, and inputting the peak derivative value to a computing means to determine the pressure in the chamber at the time that the peak derivative value was obtained.

14. A method for testing the strength of a sheet material as in claim 11, wherein the gas is air.

15. A device for testing the strength of a sheet material, comprising:
a gas reservoir having a hole therein;
a valve disposed at the reservoir hole to regulate the flow of gas from the reservoir;
a hollow member having a first hole at the first end thereof and a second hole in flow communication with the first hole, the first hole being disposed adjacent to the valve to receive a flow of gas from the reservoir;
means for measuring pressure in the hollow member and producing analog signals indicative of the pressure in the hollow member;
a sheet-positioning guide having a hole therethrough, the sheet positioning guide being spaced from and disposed opposite to the second hole; and
means operatively coupled to the pressure measuring means for determining sheet strength based on the analog signal produced at the time the sheet ruptured, wherein the means for determining sheet strength includes a computer operatively coupled to the valve to regulate the flow of gas from the reservoir, an analog-to-digital converter operatively coupled to the pressure measuring means to digitize the analog signals of the pressure measuring means, a differentiating means operatively coupled to the analog-to-digital converter to compute a derivative of each digitized pressure measurement, a peak detecting means operatively coupled to the differentiating means to detect a peak derivative value computed by the differentiating means, and a computing means operatively coupled to the differentiating means for determining the pressure in the hollow member at the time at which the peak derivative value detected by the peak detecting means was obtained.

16. A system for testing the strength of a sheet material, comprising:
a chamber having one wall consisting of the sheet material to be strength tested;
means for providing high pressure gas to the chamber, wherein the high pressure gas providing means includes a high pressure gas source, a reservoir which receives high pressure gas from the high pressure gas source, and a valve which regulates the flow of gas between the reservoir and the chamber; and
means for measuring the pressure in the chamber.

17. A system for testing the strength of a sheet material, comprising:
chamber having one wall consisting of the sheet material to be strength tested;
means for providing high pressure gas to the chamber; and
means for measuring the pressure in the chamber, wherein the pressure measuring means produces analog signals indicative of the pressure in the chamber, the device further comprising an analog-to-digital converter operatively coupled to the pressure measuring means to digitize the analog signals of the pressure measuring means, a differentiating means operatively coupled to the analog-to-digital converter to compute a derivative of each digitized pressure measurement, a peak detecting means operatively coupled to the differentiating means to determine a peak derivative value computed by the differentiating means, and a computing means to determine the pressure in the chamber at the time that the peak derivative value detected by the peak detecting means was obtained.

18. A method for testing the strength of a sheet material, comprising the steps of:
injecting high pressure gas into a chamber having one wall thereof formed of the sheet material to be strength tested;
measuring the pressure in the chamber at the time that the sheet ruptures and producing analog signals indicative of the pressure therein; and
inputting the analog signals to an analog-to-digital converter to produce digitized pressure measurements, inputting the digitized pressure measurements to a differentiating means to compute a first derivative of each digitized pressure measurement, inputting the first derivative of each digitized pressure measurement to a peak detecting means to detect a peak derivative value, and inputting the peak derivative value to a computing means to determine the pressure in the chamber at the time that the peak derivative value was obtained.

* * * * *